United States Patent [19]

Gruber et al.

[11] 4,276,136
[45] Jun. 30, 1981

[54] RADIATION CURABLE COATING COMPOSITION COMPRISING AN ETHYLENICALLY UNSATURATED OLIGOMER AND AN ETHYLENICALLY UNSATURATED COPOLYMERIZABLE ULTRA-VIOLET ABSORBER

[75] Inventors: Bruce A. Gruber, Worthington, Ohio; Donald H. Lorenz, Basking Ridge, N.J.

[73] Assignee: GAF Corporation, New York, N.Y.

[21] Appl. No.: 71,356

[22] Filed: Aug. 30, 1979

Related U.S. Application Data

[63] Continuation-in-part of Ser. No. 6,787, Jan. 26, 1979, Pat. No. 4,178,303.

[51] Int. Cl.³ .............................................. C08F 2/46
[52] U.S. Cl. ...................... 204/159.22; 204/159.15; 204/159.16; 204/159.14; 204/159.23; 526/297
[58] Field of Search .................. 204/159.22, 159.23, 204/159.14, 159.16, 159.15

[56] References Cited

U.S. PATENT DOCUMENTS

| | | | |
|---|---|---|---|
| 3,215,724 | 11/1965 | Strobel et al. | 260/465 D |
| 3,573,216 | 3/1971 | Strobel et al. | 260/465 D |
| 3,644,466 | 2/1972 | Strobel et al. | 260/465 D |
| 3,993,684 | 11/1976 | Dunnavant et al. | 260/465 D |
| 4,128,536 | 12/1978 | Brodsky et al. | 204/159.22 |

*Primary Examiner*—Harold D. Anderson
*Attorney, Agent, or Firm*—James Magee, Jr.; Walter Katz

[57] ABSTRACT

What is described herein is a radiation curable coating composition comprising:

A. An oligomer of Formula I:

$$CH_2=\overset{R^1}{\underset{|}{C}}-\overset{O}{\underset{\|}{C}}-O-Y-O-\overset{O}{\underset{\|}{C}}-\overset{R^1}{\underset{|}{C}}=CH_2 \quad (I)$$

wherein:
$R^1$ is hydrogen or methyl; and
Y is a divalent urethane residue; and

B. a copolymerizable ultra-violet light absorber which is a copolymerizable (2-cyano-3,3-diphenylacryloxy) alkylene acrylic acid ester of Formula IV:

$$\underset{(Ar)_2}{\overset{(Ar)_1}{{>}}}C=C\underset{\underset{O}{\|}{C}-OXOZ}{\overset{CN}{<}} \quad (IV)$$

where $(Ar)_1$ and $(Ar)_2$ are aromatic carbocylic nuclei of the benzene and naphthalene series;
X is $C_2$–$C_{17}$ alkylene, unsubstituted or substituted; and
Z is a copolymerizable radical selected from acryloyl, alkylacryloyl, acryloxyalkyl, acryloxyhydroxyalkyl, or alkylacryloxyhydroxyalkyl, having from $C_3$–$C_{12}$ carbon atoms.

Preferably the coating composition contains a vinyl monomer, such as N-vinyl-2-pyrrolidone or an acrylic acid ester, which is copolymerizable with the oligomer.

The process for curing the composition also is disclosed.

19 Claims, No Drawings

RADIATION CURABLE COATING COMPOSITION COMPRISING AN ETHYLENICALLY UNSATURATED OLIGOMER AND AN ETHYLENICALLY UNSATURATED COPOLYMERIZABLE ULTRA-VIOLET ABSORBER

RELATED APPLICATIONS

This application is a continuation-in-part of Ser. No. 006,787, filed Jan. 26, 1979, now U.S. Pat. No. 4,178,303, issued Dec. 11, 1979.

BACKGROUND OF THE INVENTION

1. Field of the Invention

This invention relates to radication curable coating compositions containing copolymerizable ultra-violet light absorber compounds, which can provide polymer materials with improved degradation to light.

2. Description of the Prior Art

Coating compositions which are curable under the influence of radiation in general and ultra-violet light as well as electron beam in particular are well known. Representative examples of prior coating compositions include those disclosed in U.S. Pat. Nos. 3,782,961; 3,829,531; 3,850,770; 3,874,906; 3,864,133; 3,891,523; 3,895,171; 3,899,611; 3,907,574; 3,912,516; 3,932,356; and 3,989,609. Unfortunately, these coating compositions suffer from a number of disadvantages and do not have an in situ ultra-violet absorber in the composition. Many of these coating compositions have insufficient flexibility that causes them to crack when applied to flexible substrates such as those of polyvinyl chloride. Other compositions do not adhere sufficiently to the substrate with the undesirable result that they become dislodged or peel. Still other coating compositions require the use of solvents that must be evaporated during the curing process. The evaporation of such solvents consumes energy and creates atmospheric pollution problems. Other compositions produce coatings that yellow, do not weather well, and have insufficient scratch-resistance, stain-resistance, abrasion-resistance, and/or solvent-resistance.

The use of ultra-violet absorbers in plastics or coatings to enhance weather resistance is known. The absorbers absorb the radiation and dissipate the energy and thus protect the coating from structural degradation. Considerable economic saving is realized by incorporating the ultra-violet absorber on the surface of a plastic article rather than using the ultra-violet absorber in conventional bulk application. Conventional surface application, such as the use of a solvent or paint vehicle is, moreover, undesirable in view of the pollution hazard and bulk handling procedures. Radiation curing has made possible production of coating films which are easier to handle, but heretofore ultra-violet absorbers have consumed the energy from the radiation source resulting in too high energy demands in curing or too slow curing rates. If a small amount of ultra-violet photoinitiator is used to facilitate curing, then addition of use levels of most ultra-violet stabilizers would prevent the curing from occurring.

Accordingly, it is an object of the present invention to provide an improved coating composition that is substantially free of one or more of the disadvantages of prior radiation curable coating compositions.

Yet another object is to provide a coating composition that will produce a coating that is weather-resistant, non-yellowing, scratch-resistant, stain-resistant, abrasion-resistant, and solvent-resistant.

Yet another object is to provide a coating composition that is free of volatile solvents.

Another object is to provide an improved process for coating substrates such as those of natural leather, synthetic leather, polyvinyl chloride, polyurethanes and polycarbonates.

Still another object is to provide a coating composition with a copolymerizable ultra-violet absorber which can be cured by radiation.

Other objects and advantages of the present invention will be apparent to those skilled in the art by reference to the following detailed description.

SUMMARY OF THE INVENTION

The above and other objects are accomplished according to the present invention by providing a coating composition comprising:

A. An oligomer of Formula I:

$$CH_2=C(R^1)-C(=O)-O-Y-O-C(=O)-C(R^1)=CH_2 \quad (I)$$

where:
$R^1$ is hydrogen or methyl;
Y is a divalent urethane residue; and,

B. A copolymerizable (2-Cyano-3,3-diphenylacryloxy)alkylene acrylic acid ester ultra-violet light absorber having the Formula IV:

$$\begin{array}{c}(Ar)_1\\ \phantom{xx}\diagdown\\ \phantom{xxx}C=C\\ \phantom{xx}\diagup\phantom{xxxx}\diagdown\\ (Ar)_2\phantom{xxx}\phantom{x}C-OXOZ\\ \phantom{xxxxxxxx}\|\\ \phantom{xxxxxxxx}O\end{array} \quad \begin{array}{c}CN\\ \diagup\end{array} \quad (IV)$$

where:
$(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl and naphthyl;

X is $C_2$–$C_{17}$ alkylene, unsubstituted or substituted with halo, cyano, $C_1$–$C_6$ alkyl, $C_1$–$C_6$ alkoxy, $C_1$–$C_6$ alkoxyalkyl, or $C_1$–$C_6$ alkoxyalkyleneoxy; and, Z is a copolymerizable radical selected from acryloyl, $C_3$–$C_{12}$ alkylacryloyl, $C_3$–$C_{12}$ acryloxyalkyl, $C_3$–$C_{12}$ acryloxyhydroxyalkyl, and $C_3$–$C_{12}$ alkylacryloxyhydroxyalkyl.

Preferably the composition includes a vinyl monomer or monomers which are copolymerizable with the oligomers. Suitable vinyl monomers are N-vinyl-2-pyrrolidone and acrylic acid esters.

DETAILED DESCRIPTION OF THE INVENTION

Oligomers of Formula I with an acrylic or methacrylic component are well known in the art. Oligomers of this type are shown in U.S. Pat. Nos. 3,907,574; 3,874,906; 3,989,609; and 3,895,171. A preferred type of oligomer contains both an acrylic component and a urethane portion in the Y radical. Examples of these compounds are found in U.S. Pat. Nos. 3,912,516; 3,891,523; 3,864,133 and 3,850,770.

Preferred novel types of acryl urethane are shown by Formulas II and III:

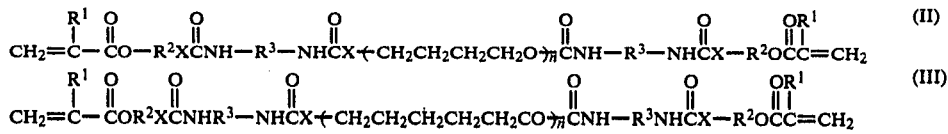

wherein:
R[1] is hydrogen or methyl;
R[2] is lower alkylene;
R[3] is aliphatic or cycloaliphatic;
X is —O— or —NH—;
n is an integer from 2 to 50 inclusive.

These oligomers are produced by reacting polytetrahydrofuran, polycaprolactone polyols and other polyols with a diisocyanate to produce an isocyanate terminated prepolymer. The isocyanate terminated prepolymer is then capped with a capping agent to produce the oligomer of Formula II and Formula III. The preferred oligomers of Formula II are those of Formula V and the preferred oligomers of Formula III are those of Formula VI:

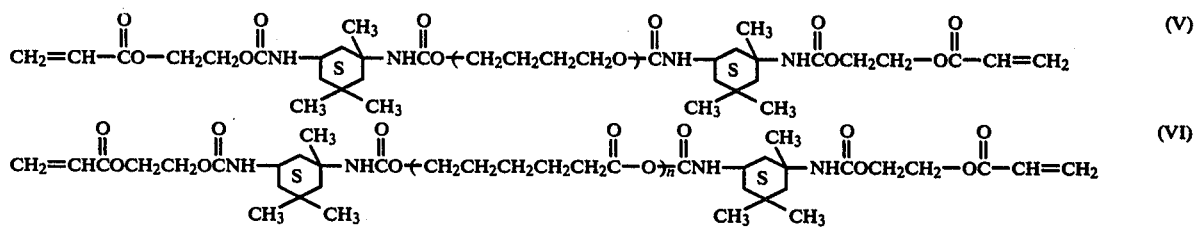

wherein "n" is an integer from 5 to 20 inclusive.

The polytetrahydrofuran is commercially available from the Du Pont Company under the tradenames "TERRECOL-650", "TERRECOL-1000", and "TERRECOL-2000", and from the Quaker Oats Company under the tradenames "POLYMEG-650", "POLYMEG-1000", and "POLYMEG-2000". In the above named tradenames the number indicates the approximate molecular weight of the polytetrahydrofuran. The most preferred polytetrahydrofuran is that having a molecular weight of 650 which is consistent with the definition of "n" in Formulas II and V herein. At higher molecular weights wherein "n" exceeds about 50 the resultant oligomer has too high a viscosity.

The caprolactone polyols are commercially available from Union Carbide Corporation under the tradenames "NIAX CAPROLACTONE POLYOLS"—PCP-0200, PCP-0210, PCP-0230, PCP-0240, PCP-0300, PCP-0301 and PCP-0310. The 0200 series are diols with molecular weights 530, 830, 1250 and 2000 respectively. The 0300 series are triols with molecular weights 540, 300 and 900 respectively.

The oligomers of Formula II, III, V and VI can be produced in accordance with U.S. Pat. No. 4,129,709. The capping agents useful in the present invention are those that will react with the isocyanate terminated prepolymer to produce the oligomers of Formula II. In general, any capping agent having a terminal amine or hydroxyl group and also having an acrylic acid or methacrylic acid moiety is suitable. Examples of suitable capping agents include among others hydroxyethyl acrylate, hydroxyethyl methacrylate, hydroxypropyl acrylate, hydroxypropyl methacrylate, hydroxybutyl acrylate, hydroxybutyl methacrylate, hydroxypentyl acrylate, hydroxypentyl methacrylate, hydroxyhexyl acrylate, hydroxyhexyl methacrylate, aminoethyl acrylate, and aminoethyl methacrylate.

The diisocyanates useful to produce oligomers of Formula II are aliphatic and cycloaliphatic diisocyanates that will react with terminal hydroxyl groups present on the polytetrahydrofuran. Of course, aromatic diisocyanates undergo the same reaction but do not yield a product as satisfactory as that obtained by the use of aliphatic diisocyanates. Examples of suitable diisocyanates include among others, isophorone diisocyanate, 4,4'-dicyclohexylmethane-diisocyanate available commercially from the Du Pont Company under the tradename "Hylene W", and trimethyl-hexamethylene-diisocyanate, 1,6 hexamethylene diisocyanate, 2,4,4 triethyl 1,6 hexylene diisocyanate, octadecylene diisocyanate and 1,4 cyclohexylene diisocyanate. The preferred diisocyanates are isophorone diisocyanate (3-isocyanatomethyl 3,5,5 trimethyl cyclohexyl isocyanate) and 4,4' dicyclohexylmethane-diisocyanate.

The vinyl monomer copolymerizable with the oligomer may be one or more monomers compatible with the oligomer selected. N-vinyl-2-pyrrolidone and acrylic acid esters having a boiling point of at least 200° C. at 760 mm Hg are preferred. These monomers allow adjustment of the viscosity for ease of coating operations and N-vinyl-2-pyrrolidones also enhance the rate of curing.

The weight ratio of oligomer to N-vinyl-2-pyrrolidone can vary widely as long as the properties of the resultant cured coating composition are not adversely affected, however, they are generally present in a weight ratio of 1:9 to 9:1 and preferably 1:3 and 3:1. At higher ratios, e.g., those rich in oligomer, the uncured coating composition tends to have too high a viscosity. This high viscosity makes it difficult to apply the uncured coating composition to the substrate. At lower ratios the resultant cured coating composition tends to be too hard and inflexible.

The acrylic acid ester should have a boiling point of at least 200° C. at 760 mm Hg. Acrylic acid esters of lower boiling points tend to vaporize during curing. Such vaporization causes undesirable changes in the coating composition. Furthermore, vaporized acrylic acid esters tend to polymerize on the radiation source, e.g., ultra-violet lamps or electron beam window. This vaporization also causes undesirable atmospheric pollution. The acrylic acid esters useful in the present invention include, among others, monoesters, diesters and higher esters of both acrylic acid and methacrylic acid. Examples of suitable acrylic acid esters include, among others, 1,4-butanedioldiacrylate, 1,6-hexanedioldiacrylate, neopentylglycoldiacrylate, pentaerythritol-tetramethacrylate, trimethylolpropanetriacrylate, ethylhexyl-acrylate, ethylhexyl-methacrylate, pentyl-acrylate, hexyl-acrylate and cyclohexyl-methylacrylate. 1,4-butanedioldiacrylate and 1,6 hexanedioldiacrylate are the preferred acrylic acid esters.

The acrylic acid ester can be present in the coating composition in widely varying amounts but is generally present in a weight ratio of 1:9 to 9:1 and preferably 1:3 to 3:1 compared to the oligomer of Formula I or II.

The copolymerizable (2-cyano-3,3-diphenylacryloxy)alkylene acrylic acid ester ultra-violet light absorber is of the Formula IV.

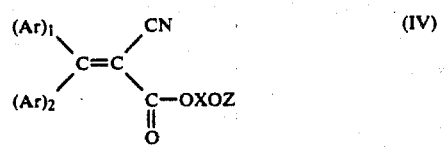

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl, phenyl, phenoxy phenyl, alkyl substituted phenoxy, or alkoxy phenyl substituted phenyl and naphthyl;

X is alkylene, $C_2$-$C_{17}$, unsubstituted or substituted with halo, cyano, alkyl, $C_1$-$C_6$ alkoxy, $C_1$-$C_6$ alkoxyalkyl, or $C_1$-$C_6$ alkoxyalkyleneoxy and;

Z is a copolymerizable radical selected from $C_3$-$C_{12}$ acryloyl, $C_3$-$C_{12}$ alkylacryloyl, $C_3$-$C_{12}$ acryloxyhydroxyalkyl, and $C_3$-$C_{12}$ alkylacryloxyhydroxyalkyl.

Suitable $(Ar)_1$ and $(Ar)_2$ groups are given in U.S. Pat. No. 3,644,466, including representative starting benzophenone compounds. In the best mode of the invention, both $(Ar)_1$ and $(Ar)_2$ are phenyl.

The X groups are unsubstituted or substituted $C_2$-$C_{17}$ alkylene radicals. The preferred groups are $C_2$-$C_6$ unsubstituted lower alkylene, which are derived synthetically from ethylene glycol, propylene glycol, butanediol and the like. Typical X groups are —$CH_2CH_2$—; —$CH_2CH_2CH_2$—; —$CH_2CH_2CH_2CH_2$—, and the like. The best mode is represented by —$CH_2$—$CH_2$—.

The Z radical is copolymerizable with vinyl monomers so that the ultraviolet absorber becomes an integral part of the polymer. Suitable Z groups are derived from acryloyl, alkylacryloyl, acryloxyalkyl, acryloxyhydroxyalkyl and alkylacryloxyhydroxyalkyl, which contain $C_3$-$C_{12}$ carbon atoms. The preferred groups are acryloyl, methacryloyl, glycidyl acryloyl and glycidyl methacryloxyl. Representative Z groups are

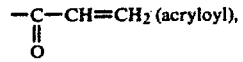

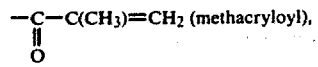

-continued

—$CH_2$—$CH(OH)CH_2OCCH$=$CH_2$ (3-acryloxy-2-hydroxypropyl),
‖
O and —$CH_2CH(OH)CH_2OCC(CH_3)$=$CH_2$
‖
O
(3-methacryloxy-2-hydroxypropyl.

The best mode is represented by acryloyl or methacryloyl.

The compounds of Formula IV contain both ultraviolet light absorber and copolymerizable groups in the same molecule. These groups are effectively separated by the X radical so that each can perform its own function without interference from the other. Thereupon, the absorber portion does not inhibit the copolymerization, and the Z radical does not affect the light absorbing properties of the molecule.

The absorber compounds may be prepared by esterification of 2-hydroxyalkyl(2-cyano-3,3-diphenyl)acrylate with an acryloyl halide or acrylic acid as described in detail in the U.S. Pat. No. 4,178,303.

Preferably, in this synthesis, the hydroxy group of a hydroxyalkyl cyano acetate first is protected by acylation with a group convertible by hydrolysis to the hydroxy compound, e.g. with acetyl chloride, to provide the corresponding acetoxyalkyl cyanoacetate. The protected compound then is condensed with a benzophenone in a Knoevenagel reaction to provide the acetoxyalkyl(2-cyano-3,3-diphenyl)acrylate in good yield. Subsequent acid hydrolysis of the protecting acetyl group affords the corresponding hydroxy intermediate, which is then directly esterified with a suitable acryloyl halide or acrylic acid to give the desired compounds.

The amount of ultra-violet absorber of the above formula in the coating compositions for radiation curing suitably can vary from 0.5 to 5%; preferably from 0.75 to 2%, and optimally, about 1.5% by weight of the composition. Lesser amounts do not give a coating that retains the light transmission or low yellowness of the coating. Greater amounts retard the curing to an unacceptable level.

If the curing is done with ultra-violet light a photo-initiator is used. Suitable photo-initiators include vicinal ketaldonyl compounds (i.e., compounds containing a ketone group and an aldehyde group) such as diacetyl, benzil; 2,3-pentanedione, 2,3-octanedione, 1-phenyl-1,2-butanedione, 2,2-dimethyl-4-phenyl-3,4-butanedione, phenyl-glyoxal, diphenyl-triketone; aromatic diketones, such as anthraquinone; acryloins, such as benzoin; pivaloin acryloin ethers, such as benzoin-methyl-ether, benzoin-ethyl-ether, benzoin-butyl-ether, benzoin-isobutyl-ether, benzoin-phenyl-ether; alpha-hydrocarbon substituted aromatic acyloins, including alpha-methyl-methyl-benzoin, alpha-alkyl-benzoin as in U.S. Pat. No. 2,722,512, and phenylbenzoin; diaryl ketones, such as benzophenone and dinaphthyl ketone; and organic disulfides, such as diphenyldisulfide. The photo-initiator can also include a synergistic agent, such as a tertiary amine, to enhance the conversion of photo-absorbed energy to polymerization initiating free radicals. Diethoxyacetophenone available from Union Carbide Corp., dimethoxyphenylacetophenone such as IRGACURE 651 available from Ciba-Geigy or a benzoin ether such as Vicure 10 available from Stauffer Chemical Company are preferred. The photo-initiator is present in the coating composition in an amount sufficient to initiate the desired polymerization under the influence of the amount of actinic light energy absorbed. The coating composition generally contains from 0.01 to 5 weight percent of photo-initiator based on the weight of the coating composition.

The coating composition can also contain an addition polymerization inhibitor to prevent undesirable auto-polymerization of the coating composition in storage prior to use. Examples of suitable addition polymerization inhibitors, include, among others, di(1,4 sec-butylamino)benzene available from the DuPont Company under the tradename "Anti-Oxidant 22" and phenothiazine available from Tefenco Chemical Co. The addition polymerization inhibitor is present in an amount sufficient to prevent auto-polymerization and is generally present in an amount from 100–300 PPM based on the weight of the coating composition.

The coating composition can also contain a surfactant. The preferred surfactants are silicone surfactants such as that available from the Dow Corning Corporation under the tradename "DC-193". The surfactant is present in an amount necessary to reduce the surface tension of the coating composition and reduce its viscosity to the desired level. The surfactant generally comprises from 0.1 to 5 weight percent based on the weight of the coating composition.

The coating compositions of the present invention can also contain other conventional additives, such as flow control and leveling agents, organic and inorganic dyestuffs and pigments, fillers, plasticizers, lubricants and reinforcing agents, such as alumina, silica, clay, talc, powdered glass, carbon black and fiberglass.

The coating compositions of the present invention can be cured by applying them as a film 0.5 mil thick on the substrate. Curing is preferably done under an inert atmosphere of nitrogen. The coating composition may be applied as a thin film in any conventional manner such as by spraying, brushing, dipping, roll coating and the like.

Conventionally, the film on the substrate is positioned to travel on a conveyor and pass under a source of a free radical generator, such as radiation. The coated side of the substrate is exposed to the radiation for a time sufficient to effect polymerization and convert the film into an adherent, tough, flexible coating.

As used herein the term radiation refers to any radiation source which will produce free radicals and induce addition polymerization of vinyl bonds. The actinic radiation is suitably in the wave length of 2000–7500 A, preferably 2000 to 4000. A class of actinic light useful herein is ultra-violet light and other forms of actinic radiation are from the sun, artificial sources such as Type RS sunlamps, carbon arc lamps. Xenon arc lamps. mercury vapor lamps, tungsten halide lamps, lasers, fluorescent lamps with ultra-violet light emitting phosphors.

Ultra-violet curing rates greater than 20 ft/min/lamp must be obtained in order to be commercially acceptable. With a reasonable thickness (less than 10 mils) coating compositions with the ultra-violet absorber of Formula IV, present in an amount from 0.5 to 3% based on the weight of the composition, can be cured at rates of 25–50 ft/min/lamp.

The preferred electron beam system contains a wide curtain of electrons directly from a linear cathode. A curtain of electrons from the gun's cathode, accelerated to a high velocity by a 200 KV potential, emerges from the chamber through a foil window into the coated substrates (Electroncurtain TM by Energy Sciences, Inc.).

The electron beam curing of the coating compositions as described above is cured at less than 5 Mrads and generally at 2 Mrads. Curing at greater than 8 Mrads is deemed unacceptable because of the high cost.

Laminates of film coatings based on acryl urethanes with an ultra-violet absorber of (2-cyano-3,3-diphenylacryloyloxy)alkylene acrylic acid ester applied on clear polyvinylchloride are surprisingly non-leachable and do not yellow.

The invention is further illustrated by the following examples in which all parts and percentages are by weight unless otherwise indicated. These non-limiting examples are illustrative of certain embodiments designed to teach those skilled in the art how to practice the invention and to represent the best mode contemplated for carrying out the invention.

EXAMPLE 1

Preparation of Radiation Cured Coating

Into a dry 1 l. resin kettle fitted with an air inlet tube, a stirrer, thermometer, and dropping funnel was charged 300.8 g. (1.3 moles) of isophorone diisocyanate and 4.8 ml. of a 10% (W/V) solution of dibutyltin dilaurate catalyst in ethylhexylacrylate. Dry air then was bubbled through the stirred solution while 322.1 g. (0.61 moles) polyolcaprolactone (PCP-200) was added dropwise over 45 minutes. The solution then was heated to 80° C. and the reactants maintained at this temperature for 30 minutes. After cooling to 55° C., 160 mg. of phenothiazine was admixed. Then 151.9 g. (1.3 moles) of hydroxyethyl acrylated was added rapidly. The temperature was raised to 80° C. and maintained for 2 hours.

The resulting oligomer (58.1 g.) was formulated for coating by mixing with 25.4 g. of ethylhexylacrylate, 16.8 g. of vinyl pyrrolidone, 14.2 g. of hexanediol diacrylate, 1.8 g. of DC-193 silicone surfactant, 2.4 g. of Vicure-10 photo-initiator and 2.5 g. of 2-(2-cyano-3,3-diphenylacryloxy)ethyl acrylate. The resulting syrup was coated onto a polyvinyl chloride plate to form a film having a thickness of 1.5 mil. The film then was cured by ultra-violet radiation under an inert atmosphere to provide a tough, clear coating containing the copolymerized UV absorber compound. The thus-protected polyvinyl chloride plate showed little tendency to yellowing even after 734 hours of testing in a Weather-Ometer.

Although the invention has been described in considerable detail with reference to certain preferred embodiments thereof, it will be understood that variations and modifications can be effected within the spirit and scope of the invention as described above and as defined in the appended claims.

What is claimed is:

1. A radiation curable coating composition comprising:

A. An oligomer of Formula I:

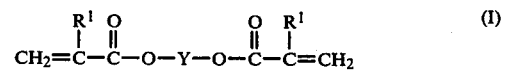

wherein:

$R^1$ is hydrogen or methyl; and

Y is a divalent urethane containing radical produced from a polyol and a diisocyanate; and B. a copolymerizable ultra-violet light absorber compounds of Formula IV:

$$\begin{array}{c}(Ar)_1\\ \phantom{(Ar)}\diagdown\\ \phantom{(Ar)}C=C\\ \phantom{(Ar)}\diagup\\ (Ar)_2\end{array}\begin{array}{c}CN\\ \diagup\\ \diagdown\\ C-OXOZ\\ \|\\ O\end{array}\quad(IV)$$

where:

(Ar)$_1$ and (Ar)$_2$ are aromatic carbocyclic nuclei of the benzene and naphthalene series and are independently selected from the group consisting of phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl and naphthyl;

X is $C_2$–$C_{17}$ alkylene, unsubstituted or substituted with halo, cyano, $C_1$–$C_6$ alkyl, $C_1$–$C_6$ alkoxy, $C_1$–$C_6$ alkoxyalkyl, or $C_1$–$C_6$ alkoxyalkyleneoxy; and Z is a copolymerizable radical selected from the group consisting of acryloyl, $C_3$–$C_{12}$ alkylacryoyl, $C_3$–$C_{12}$ acryloxyalkyl, $C_3$–$C_{12}$ acryloxyhydroxyalkyl, and $C_3$–$C_{12}$ alkylacryloxyhydroxyalkyl.

2. The coating composition of claim 1 further comprising a vinyl monomer copolymerizable with the oligomer.

3. The coating composition of claim 1 further comprising an addition polymerization inhibitor present in an amount sufficient to avoid the auto-polymerization of the composition during storage.

4. The coating composition of claim 3 wherein the addition polymerization inhibitor is present in an amount from 100–300 parts per million weight percent based upon the weight of the composition.

5. The coating composition of claim 3 wherein the weight ratio of oligomer to vinyl monomer is from 1:9 to 9:1.

6. The coating composition of claim 1 further comprising a photo-initiator present in an amount sufficient to initiate the desired polymerization under the influence of the amount of actinic light energy absorbed.

7. The coating composition of claim 1 wherein the ultra-violet light absorber is present in an amount from 0.5 to 5 weight percent based on the weight of the composition.

8. A composition according to claim 1 in which in Formula IV both (Ar)$_1$ and (Ar)$_2$ are phenyl.

9. A composition according to claim 1 in which in Formula IV X is $C_2$–$C_6$ alkylene.

10. A composition according to claim 1 in which in Formula IV, Z is acryloyl, methacryloyl, 3-acryloxy-2-hydroxypropyl, or 3-methacryloxy-2-hydroxypropyl.

11. A composition according to claim 1 in which in formula IV (Ar)$_1$ and (Ar)$_2$ are phenyl, X is $C_2$–$C_6$ alkylene, and Z is acryloyl, methacryloyl, 3-acryoxy-2-hydroxypropyl, or 3-methacryloxy-2-hydroxypropyl.

12. A composition according to claim 1 in which the absorber compound is 2-(2-cyano-3,3-diphenylacryloxy)ethyl acrylate.

13. A composition according to claim 1 in which the absorber compound is 2-(2-cyano-3,3-diphenylacryloxy)ethyl methacrylate.

14. A composition according to claim 1 in which the absorber compound is 3-(2-cyano-3,3-diphenylacryloxy)propyl acrylate.

15. A composition according to claim 1 in which the absorber compound is 4-(2-cyano-3,3-diphenylacryloxy)butyl acrylate.

16. A composition according to claim 1 in which the absorber compound is 3-(2-cyano-3,3-diphenylacryloyloxy)-2-hydroxypropyl acrylate.

17. A composition according to claim 1 in which the absorber compound is 3-(2-cyano-3,3-diphenylacryloyloxy)-2-hydroxypropyl methacrylate.

18. A coating composition of claim 1 which is photopolymerizable in the presence of ultra-violet light to produce an adherent coating that is weather-resistant, flexible, scratch-resistant, stain-resistant, abrasion-resistant, and solvent-resistant, said coating composition consisting essentially of:

A. an oligomer of Formula II:

$$\underset{\text{(II)}}{\overset{R^1\ O\qquad\ O\qquad\qquad O\qquad\qquad\qquad\qquad O\qquad\ O\quad OR^1}{\underset{|\ \|\qquad\ \|\qquad\qquad\|\qquad\qquad\qquad\qquad\|\qquad\ \|\quad|}{CH_2=C-CO-R^2XCNH-R^3-NHC(\!\!+\!\!CH_2CH_2CH_2CH_2O)_{\overline{n}}CNH-R^3-NHC-R^2OCC=CH_2}}}$$

wherein:

R$^1$ is hydrogen or methyl;

R$^2$ is lower alkylene;

R$^3$ is aliphatic or cycloaliphatic;

X is —O— or —NH—;

n is an integer from 2 to 50 inclusive;

B. N-vinyl-2-pyrrolidone;

C. hexanediol diacrylate;

D. 2-(2-cyano-3,3-diphenylacryloxy)ethyl acrylate present in an amount from 0.5 to 5 weight percent based on the weight of the composition;

E. a photo-initiator present in an amount from 0.01 to 5 weight percent based on the weight of the composition;

F. an addition polymerization inhibitor present in an amount from 100–300 PPM based on the weight of the composition;

G. a silicone surfactant present in an amount from 0.1 to 5 percent based on the weight of the composition, wherein the ratio A:B is from 1:3 to 3:1, and wherein the ratio A:C is from 1:3 to 3:1.

19. A coating composition of claim 1 which is photopolymerizable in the presence of ultra-violet light to produce an adherent coating that is weather-resistant, flexible, scratch-resistant, stain-resistant, abrasion-resistant and solvent-resistant, said coating composition consisting essentially of:

A. an oligomer of Formula III:

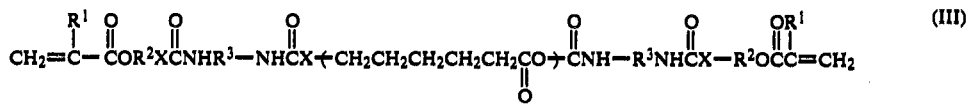

wherein:
R¹ is hydrogen or methyl;
R² is lower alkylene;
R³ is aliphatic or cycloaliphatic;
X is —O— or —NH—;
n is an integer from 2 to 50 inclusive;
B. N-vinyl-2-pyrrolidone;
C. hexanediol diacrylate;
D. 2-(2-cyano-3,3-diphenylacryloxy)ethyl methacrylate, present in an amount from 0.5 to 3 weight percent based on the weight of the composition.

E. a photo-initiator present in an amount from 0.01 to 5 weight percent based on the weight of the composition;
F. an addition polymerization inhibitor present in an amount from 100–300 PPM based on the weight of the composition;
G. a silicone surfactant present in an amount from 0.1 to 5 percent based on the weight of the composition,
wherein the ratio A:B is from 1:3 to 3:1; and
wherein the ratio A:C is from 1:3 to 3:1.

* * * * *